(12) United States Patent
Bourhis et al.

(10) Patent No.: US 12,324,933 B2
(45) Date of Patent: Jun. 10, 2025

(54) DEVICE FOR ULTRA-HIGH DOSE RATE RADIATION TREATMENT

(71) Applicants: CERN—EUROPEAN ORGANIZATION FOR NUCLEAR RESEARCH, Geneva (CH); CENTRE HOSPITALIER UNIVERSITAIRE VAUDOIS (C.H.U.V.), Lausanne (CH)

(72) Inventors: Jean Francois Marie Bourhis, Corseaux (CH); Marie-Catherine Sophine Vozenin, Etoy (CH); Jean-Francois Germond, Chez-le-Bart (CH); Walter Wuensch, Onex (CH); Steinar Stapnes, Versoix (CH); Alexej Grudiev, Duillier (CH)

(73) Assignees: CERN—EUROPEAN ORGANIZATION FOR NUCLEAR RESEARCH, Geneva (CH); CENTRE HOSPITALIER UNIVERSITAIRE VAUDOIS (C.H.U.V.), Lausanne (CH)

( * ) Notice: Subject to any disclaimer, the term of this patent is extended or adjusted under 35 U.S.C. 154(b) by 226 days.

(21) Appl. No.: 17/761,800

(22) PCT Filed: Sep. 24, 2020

(86) PCT No.: PCT/EP2020/076662
§ 371 (c)(1),
(2) Date: Mar. 18, 2022

(87) PCT Pub. No.: WO2021/058624
PCT Pub. Date: Apr. 1, 2021

(65) Prior Publication Data
US 2022/0387824 A1 Dec. 8, 2022

(30) Foreign Application Priority Data
Sep. 26, 2019 (EP) .................................. 19199864

(51) Int. Cl.
*A61N 5/10* (2006.01)

(52) U.S. Cl.
CPC .... *A61N 5/1077* (2013.01); *A61N 2005/1087* (2013.01); *A61N 2005/1089* (2013.01)

(58) Field of Classification Search
None
See application file for complete search history.

(56) References Cited

U.S. PATENT DOCUMENTS

| 10,576,303 B2 * | 3/2020 | Bharadwaj | A61N 5/1064 |
| 2002/0090194 A1 * | 7/2002 | Tajima | G21K 1/003 250/398 |

(Continued)

FOREIGN PATENT DOCUMENTS

WO WO-2015102680 A2 7/2015

OTHER PUBLICATIONS

Subiel, A., et al., "Challenges of dosimetry of ultra-short pulsed very high energy electron beams," Physica Medica, 42: 327-331 (2017).

(Continued)

*Primary Examiner* — Marcus H Taningco
(74) *Attorney, Agent, or Firm* — Harness Dickey & Pierce P.L.C.

(57) ABSTRACT

The present relates to device for ultra-high dose rate radiation treatment to a patient, comprising: —a radiation source for providing a radiation beam, and—a linear accelerator for accelerating said radiation beam until a predetermined energy, and—a beam delivery module for delivery the accelerated radiation beam. The device is arranged for generating an accelerated radiation beam having a predetermined energy between about 50 MeV and about 250 MeV, to deliver rate radiation dose of at least 10 Gy, during an overall time less than about 200 ms in order to generate a (Continued)

radiation field for treating a target volume of at least about 30 cm3, with said ultra-high dose rate radiation dose and/or a target volume located at least about 5 cm deep in the tissue of the patient with said ultra-high dose rate radiation dose.

17 Claims, 5 Drawing Sheets

(56) References Cited

U.S. PATENT DOCUMENTS

2016/0287905 A1    10/2016  Liger
2018/0280734 A1*   10/2018  Clayton ............... A61N 5/1083

OTHER PUBLICATIONS

International Search Report from corresponding PCT Application No. PCT/EP2020/076662 dated Dec. 3, 2020.
Written Opinion from corresponding PCT Application No. PCT/EP2020/076662 dated Dec. 3, 2020.

* cited by examiner

DEVICE FOR ULTRA-HIGH DOSE RATE RADIATION TREATMENT

PRIORITY STATEMENT

This application is a national stage application under 35 U.S.C. § 371 of PCT International Application No. PCT/EP2020/076662, which has an international filing date of 24 Sep. 2020 and claims priority under 35 U.S.C. § 119 to European Patent Application No. 19199864.0 filed on 26 Sep. 2019. The contents of each application recited above are incorporated herein by reference in their entirety.

TECHNICAL FIELD

The present invention relates to a device for ultra-high dose rate radiation treatment.

BACKGROUND OF THE ART

Cancer is a dominant worldwide cause of death, mainly treated by surgery, radiotherapy (RT) and chemotherapy. There is a rapid increase of its incidence but only a slow improvement in curability, despite recent progress notably in immunotherapy, robotics surgery, and the introduction of new molecular targeted drugs.

Since the pioneered work of Roentgen and Marie Curie in the early 20$^{th}$ century, radiotherapy remains an essential tool for treating cancer. Although recent development in radiotherapy allowed these treatments to be more precise and more effective, the remaining side effects are still a problem that limits its use, for instance damages to healthy tissue.

Delivering high curative radiation doses to tumors depends on the ability to spare normal tissues from harmful effects of radiation. Over the last century, both fractionation and precise volume optimization appeared as the most powerful tools to obtain a differential effect between normal tissues and tumors thereby minimizing the side effects.

An alternative and complementary emerging solution to limit radiation-induced damage on normal tissue is to reduce the irradiation time in so-called FLASH Radiotherapy (RT) or FLASH Therapy. A conventional radiotherapy treatment generally aims at administering a total dose of 20 to 70 Gy to each tumor, typically in doses of 2 Gy per fraction, each fraction being administered over several minutes. During the past few years, a number of experiments have been carried out which demonstrate that RT with ultra-short irradiation times (below 100 ms) can significantly reduce the side effects. Notably, it has been shown that when radiation is delivered in a few ultra-intense pulses with very high dose and ultra-high dose rate in the pulse (typically a dose per pulse above 1.5 Gy and mean dose rate above 10$^6$ Gy within pulse), healthy tissue are spared while tumor tissue response remains unchanged, resulting in a more effective treatment.

The document "Treatment of the first patient with FLASH RT" from J. Bourhis et al, Radiotherapy and Oncology, 2019, Radiother Oncol., 2019 Jul. 11, S0167-8140(19) 32959-7 relates pioneered clinical use of FLASH RT treatment. This document discloses the use of existing RT apparatus to treat a superficial skin tumor with 5.6 MeV electrons to give a dose of 15 Gy in 10 pulses each of 1 µsecond for an overall irradiation time of 90 ms, corresponding to an average dose rate of 150 Gy/sec. Compared to the skin reaction after exposure to conventional RT using 20-21 Gy fractionated irradiation, the FLASH RT reactions associated with the administration of 15 Gy in 90 ms were minimal. This experience showed the technical feasibility and clinical safety of delivering a high single dose to a patient instead of an equivalent conventional dose fractioned over several minutes irradiation.

A first key aspect of FLASH RT stands with the dose rate of the radiation beam: a high radiation dose, that is generally fractionated and given in several minutes in conventional RT must be given in a very limited fraction of a second in FLASH RT, typically in the range of milliseconds. A second key aspect of FLASH RT is that an effective sparing of healthy tissues in large fields irradiation (above or equal to 10 cm) requires shorter delivery times, compared the one described until now and needed for obtaining FLASH sparing of healthy tissues in small irradiation fields (in the range of few cm).

It is known that electrons lose approximately 2 MeV/cm in water so a radiation beam of around 6 MeV can only be used for treating skin tumor or other superficial tumor. For this reason electrons beam are generally not used for treating tumors situated deep in the body. The treatment of deep seated tumors with FLASH electrons would require a much higher energy electrons beam, for instance in the range of 30 to 250 MeV or higher.

A further issue occurs when it comes to treating large volume of tumors with RT or FLASH RT. The existing RT instruments are not capable of treating large volumes with FLASH RT since the generated radiation beam do not have the required characteristics to deliver the required dose in FLASH conditions.

Overall, when it comes to treating deep seating tumor and/or large tumor with FLASH RT, the existing technologies do not provide satisfying solutions notably because they are not suitable for generating—ultra high dose rate electron beam with the required energy to treat large and/or deep seated tumor.

SUMMARY OF THE INVENTION

The above problems are solved by the device and the method according to present invention.

The invention concerns a device for ultra-high dose rate radiation treatment to a patient, the device comprising:
  a radiation source for providing a radiation beam, and
  a linear accelerator for accelerating said radiation beam until a predetermined energy, and
  a beam delivery module for delivering the accelerated radiation beam from said linear accelerator toward the patient to treat a target volume with a radiation dose,
  characterized in that the device is arranged for generating an accelerated radiation beam having a predetermined energy between about 50 MeV and about 250 MeV, more preferably between about 120 MeV and about 150 MeV, to deliver an ultra-high dose rate radiation dose of at least about 10 Gy, preferably up to about 25 Gy, preferably up to about 35 Gy, more preferably up to about 40 Gy, during an overall time less than about 200 ms, preferably less than about 100 ms, preferably less than about 50 ms, preferably less than about 10 ms, so that the device is arranged for generating a radiation field for treating a target volume of at least about 30 cm$^3$, preferably between about 30 cm$^3$ and about 1000 cm$^3$ with said ultra-high dose rate radiation dose and/or a target volume located at least about 5 cm deep in the tissue of the patient, preferably between about 5 cm and about 25 cm, with said ultra-high dose rate radiation dose.

In the present invention, the device allows to generate an accelerated radiation beam of at least about 50 MeV and about 250 MeV, more preferably between about 120 MeV and about 150 MeV. With this remarkably high energy and total charge of the generated accelerated beam, a radiation dose up to about 25 Gy, up to about 35 Gy, more preferably up to about 40 Gy can be delivered in an overall time of milli-second range.

In a preferred embodiment, the device is arranged for generating an accelerated radiation beam having a predetermined energy between about 50 MeV and about 250 MeV, more preferably between about 120 MeV and about 150 MeV, to deliver an ultra-high dose rate radiation dose of at least about 10 Gy, preferably up to about 25 Gy, preferably up to about 35 Gy, more preferably up to about 40 Gy, during an overall time less than about 200 ms, preferably less than 100 ms, preferably less than 50 ms, preferably less than about 10 ms.

In an embodiment, the overall time is less than about 1 ms.

When it comes to generate large radiation field in FLASH condition (ultra-high dose rate) for example for a target volume of at least about 30 cm$^3$, preferably between about 30 cm$^3$ and about 1000 cm$^3$, more preferably between about 30 cm$^3$ and at least about 1000 cm$^3$, the existing instruments are not capable of delivering the required dose in FLASH condition, notably because the accelerated beam is not powerful enough to provide the required dose to the whole target volume in an overall time of milli-second range duration. This is also true when the target volume is located at least about 5 cm deep in the tissue of the patient, the existing device fail to provide ultra-high dose rate radiation (i.e. FLASH).

The energy of an electron beam determines the depth of penetration into water or tissue. If one considered the existing FLASH therapy using a 6 MeV radiation beam, there is 85% of the dose at 2 cm. Beyond 2 cm, the attenuation of the beam is very strong, so that a target volume cannot be treated in FLASH conditions anymore. In other words, the level of energy of the radiation beam depends on how deep in tissue is located the target volume. That is why, the existing devices can only be used to treat superficial target volume in FLASH conditions.

In the present invention, the accelerated high energy beam is suitable for delivering the required dose to the whole target volume whether to a large target volume, or a deep seated target volume. For example, with a 30 MeV radiation beam, we find 85% of the dose at about 10 cm depth. As a result, very energetic beams of this type are equivalent to high energy megavoltage X-ray in terms of penetration capacity. Increasing the energy of the radiation beam allows to adjust the penetration depth. There is a need to have a radiation beam of at least 30 MeV to target large target volume or deep seated target volume. A radiation beam comprised between 50 MeV and 150 MeV generally gives the necessary depth for any patient, although there is no energy upper limit. Irradiating in FLASH conditions at these energies has never been achieved in patients and even more for large fields (diameter above 10 cm).

Advantageously, the present invention provides remarkably less side effects in healthy tissue compared to conventional RT, while maintaining intact the effect on tumors.

With the present invention, due to the very short treatment times and to the possibility to control or tune the accelerated beam delivery thanks to the beam delivery means (for instance bend electrons beams with magnets), it is possible to switch the accelerated beam easily from one room/one patient to another. The present invention is a cost effective apparatus since a single acceleration beam line can serve a large number and possibly unlimited treatment rooms. It can delivered the required dose to a great number of patient successively.

In the present invention, there is a major increased efficacy on multi-resistant tumors due to the capacity to deliver more biological equivalent dose (BED) to large tumors compared to conventional RT. As an example, the characteristics of the present invention which allow a FLASH sparing effect on healthy tissue of about 33% of the prescribed dose were integrated in a treatment planning system and compared to conventional RT. This translated in the possibility to deliver safely to a patient a single FLASH dose of 28 Gy whereas the same patient and the same tumor have been treated with palliative conventional radiotherapy of 46 Gy in 23 fractions. The biological equivalent dose (BED) for the tumor of this 28 Gy single dose irradiation is above 100 Gy which is known as being highly curative, especially compared to the conventional 46 Gy which was really given.

Advantageously, the present invention offers the possibility to treat a patient with the required curative dose with an overall number of radiotherapy fractions markedly reduced compared to conventional RT. For instance, a total dose of 28 Gy can be administered in one single FLASH fraction, whereas with conventional RT, it would require multiple fractions (typically about 12 or 14 fractions). In conventional RT, there is need to monitor tumor motion during radiotherapy to reduce the margin around the tumors and limit the volume of healthy tissues exposed to high dose radiation. In the present invention, the ultra-fast delivery of the dose in the range of milliseconds makes the motion management of tumor during irradiation irrelevant. It also allows higher conformality for the beams delivery and hence a more effective sparing of healthy tissues.

In particular, the accelerated beam (i.e. radiation beam) is a very high energy electron (VHEE) beam with a charge of at least about 1000 nC, preferably at least about 1500 nC. Advantageously, the dose is directly proportional to the charge. In the present invention, the device is configured to provide a high charge of at least 1000 nC and thus a high dose.

The device according to the present invention can comprise two complementary means to achieve high conformality of the dose distribution:
1) several beams lines (preferably two or three such that FLASH conditions are preserved) converging simultaneously from different angles and/or different angles used from one fraction to another;
2) shaping each beam line individually.

This allows to keep high conformality while adding FLASH characteristics on top of it.

In a preferred embodiment, the beam delivery module comprises separating means for separating the accelerated radiation beam, named single accelerated beam, in a plurality of accelerated beam lines with a radiation dose of about 7 Gy per beam, preferably about 10 Gy per beam, more preferably about 20 Gy per beam delivered during said overall time.

In an embodiment, the linear accelerator is arranged for generating a single accelerated beam comprising multiple trains of particles bunches, preferably two or three trains of particles bunches, the beam delivery module comprises separating means for separating the single accelerated radiation beam in a plurality of accelerated beam lines separated by a determined angle, and subsequently focusing each of said beam lines toward the patient to arrive simultaneously on the target volume, each beam line corresponding to a train of particles bunches.

Advantageously, in this embodiment the linear accelerator is arranged for accelerating and transporting various part of the beam at discrete energies. In conventional therapy the patient is radiated from many angles to achieve the required conformality. This is done by rotating the radiation source around the patient. In FLASH conditions, i.e. duration of maximum a few ms, there is not enough time to move large objects. Instead in the present embodiment, we come from for instance two to three trajectories within the FLASH time scale to achieve the required conformality. For example in the overall treatment time in the range of ms (milli second), the first half of the accelerated beam comes from one direction then the second half from another. In the present invention, instead of moving objects we can propagate the beam through different beam lines by accelerating the beam to different energies. The energies differ for instance by a minimum of about 10% which is enough to separate them in a dipole magnet. The overall energy is preferably chosen by clinical considerations.

Advantageously, the accelerated radiation beam can be split in several beam lines. The accelerated beam radiation can arrive to the patient from one or several directions simultaneously (in the range of a few ms) in a single treatment. The advantage of splitting the beam is to achieve high conformality for delivering the dose to the tumor.

In a preferred embodiment, the inventors discovered that three (3) and preferably two (2) simultaneous beams converging in the target volume provide very satisfying results to achieve both high conformality on the tumor together with an optimal FLASH sparing of healthy tissues all along the track (i.e. trajectory) of each individual beam (the sparing of healthy tissues by FLASH better operates at high dose i.e. superior to 10 Gy per beam), for instance for delivering a total dose of 20 Gy.

FLASH effect is needed to spare healthy tissues in large volumes. FLASH can essentially be observed at high dose per fraction, which means that in order to achieve effective sparing of normal tissues along each beam, it is important to have only very few beams converging in the tumor. For instance 20 Gy given in two beams should maintain the FLASH sparing effect all along the tracks of each beam if only 2 beams are used (10 Gy each) or if 3 beams are used (7 Gy each) but if more beams are used then FLASH sparing effect along the tracks of each beam should disappear (below 7 Gy it should disappear). Advantageously, when there is two or three beams, the device combines the possibility to get optimal FLASH sparing effect along with very good dose distribution conformality. Both high conformality and FLASH will then contribute to effective sparing of normal tissues, whereas in the existing device, only high conformality can be used.

In particular, if more than one, for instance two fractions are used, the beam arrangement in terms of ballistics could be different from one fraction to another for instance simply by moving the patient coach by 90°. Then conformality can be increased.

In an embodiment, each train has energy which differs by a minimum of about 10%, and/or each beam line having an energy of at least about 50 MeV.

In one embodiment, the separating means are chosen among the list comprising energy-based separating means by using magnetic spectrometer, radio frequency deflector based means.

In one embodiment, a radio frequency deflector is used to separate the accelerated beam in beam lines along different trajectories. In this embodiment a single energy beam can be separated in a several beam lines.

In one embodiment, each train of particles bunches has energy which differs by a minimum of approximately 10% and the separation of trajectories in the beam delivery system is made using a magnetic spectrometer.

To separate by energy using magnetic spectrometer, the linear accelerator accelerates and transports the beam to the beam delivery system with two or more energies. These energies differ preferably by a minimum of approximately 10%. For instance, this is be done from one train of particles bunches to another train of particles bunches (for instance there are approximately 10 trains of particles bunches per treatment) by varying input radio frequency power level. Alternatively, it can be done within a radio frequency pulse by varying the radio frequency phase on which the bunch sits. The different energy beams are deflected by different angles in the first dipole as in a magnetic spectrometer. The beams then follow distinct paths to converge simultaneously (in the range of few ms) on the target volume.

A higher energy beam is bent relatively less than a lower energy beam in a dipole magnet. All the trains of particles bunches come out the linear accelerator along the same line but are bent by different angles in the first dipole. By giving some length they travel on trajectories away from each other. At a sufficient distance they can be bent back towards the patient converging on the tumor.

Advantageously, energy-based separating means by using magnetic spectrometer is a preferred solution, for instance because it is a cheaper than radio frequency deflector based means.

A beam delivery module with radio frequency deflector(s) uses radio frequency fields to deflect the beam instead of a static magnetic field. It is pulsed in the same way as the linear accelerator so each train can be deflected separately.

In particular, after separation in the main dipole, the accelerated radiation travels along distinct beam lines. After bending the radiation back to the patient, these beam lines converge on the tumor separated by angles, typically from 30 to 90 degrees, more preferably between 30° and 60°, in particular 30° and 60°. Preferably, the bending element of each beam line directs a beam line toward the patient along a determined angle. The full optimization of the number and of the angles of beams is chosen in conjunction with clinical dose distribution considerations.

It is known that in RT and particle therapy, it is advantageous to provide the dose from different directions to the target volume in order to achieve optimal conformality of the dose distribution. In conventional RT instrument, a moving linear collimator is used to optimize the dose provided to the target volume. However, a mechanical movement is not possible in the FLASH times scales (millisecond range, i.e. ms range). In an embodiment, the solution of the present invention is to provide distinct beam lines, preferably 2 or 3, that will converge exactly at the same place in the target volume and at the exact same time, i.e. in the range of a few milli seconds. This allows to spare the healthy tissues both through high conformality for beam delivery and through a FLASH effect.

The number of paths, i.e. beam lines, is preferably two or three since with more paths/beam lines, the FLASH effect that operates essentially at high dose per fraction would be significantly reduced or totally suppressed.

Advantageously, the present invention can have two means which are both complementary to achieve optimal conformality of the dose distribution; the first is controlling the shape of each accelerated beam line and the second is splitting the initial beam into several beam lines that are simultaneously converging in the tumor. Overall the present invention has the unique capacity of providing highly conformal radiation delivery along with optimal parameters needed for treating large tumors in FLASH mode.

In one embodiment, the device comprises beam shaping means for controlling the conformal irradiation of the beam arriving on the target volume, for instance shaping means in the delivery system, preferably after the linear accelerator. For instance, the beam shaping means comprise focusing means providing a control of the traverse size of the accelerated beam or accelerated beam line(s) to achieve optimal shaping of the beam and optimal treatment conformality for target volumes with complex shapes.

It is possible to have multiple means to control the transverse beam profile. For instance, each main element of the device can have beam collimation, i.e. beam in the radiation source (i.e. injector), in the linear accelerator (i.e. linac) and in the beam delivery system. Collimation in the radiation source and linear accelerator will give the same shape, typically circle, to the different beam lines while collimation in the beam delivery system gives independent shapes to the different lines. The final focusing quadrupoles in the beam delivery system can also be used to adjust focal shape, for instance from circles to ellipses. Preferably the most important collimation should be the one at the end of the linear accelerator, and it is possible to have a device with only this collimation.

In an embodiment, said radiation dose comprises radiation pulses of accelerated radiation beam, each radiation pulse comprising at least one particles bunch, the device being arranged for delivering the ultra-high-dose rate radiation dose with at least about 2 Gy per radiation pulse, preferably at least about 5 Gy per radiation pulse, more preferably at least about 10 Gy per radiation pulse, with a dose rate in the radiation pulse of at least about $10^6$ Gy/sec, preferably at least about $10^7$ Gy/sec and preferably with a total number of radiation pulses below 10, more preferably below 3. Thus, the device is arranged for delivering in FLASH conditions needed for obtaining a FLASH effect even in large field irradiation (above or equal to 10 cm), and overall treatment time for a dose of 25 Gy in the range of few milliseconds (below 50 ms and preferably below 10 ms) and a total number of radiation pulses below 10 and preferably below 3.

In an embodiment, the device is arranged for delivering the dose with a homogeneity (in other word uniformity) of target volume coverage of at least about 85%. Advantageously, homogeneity could be achieved by a combination of the radiation source design (for instance specifically the shape of the laser spot profile in the injector) linear accelerator design (for instance the focusing lattice and control of wakefields) and the delivery module (for instance expanding the beam and collimation at the end of the linear accelerator). For instance, collimation is passing the beam through an aperture cutting off the outer parts and giving a well defined shape to the beam.

In one embodiment, the radiation source is an electron source. Thus, the dose is delivered to the patient in the form of electrons.

Preferably, the radiation source is a high current electron source.

In one embodiment, the radiation source is an electron source, the device further comprising a conversion module for converting the electron beam into a photon beam.

Thus, the dose is delivered to the patient in the form of photons.

In one embodiment, the radiation source is a proton source. Thus, the dose is delivered to the patient in the form of proton.

In an embodiment, the radiation source (2) is arranged for delivering the radiation dose in sequence of train of particles bunches with a capability of up to ten trains of particles bunches of 250 nC each in said overall time.

In one embodiment, the radiation source is chosen among a list comprising a radio-frequency laser-driven injector (named rf gun), a thermionic injector.

The rf gun consists of a radio frequency cavity system (S, C or X-band) and a short-pulse (1-2 ps) laser system. The laser strikes the cathode of the cavity system and emits the electron bunches of approximately 1 nC. The beam is accelerated for instance up to about 5 MeV.

A thermionic injector is based on a continuous electron beam generated by a heated cathode, through thermionic emission. The beam is bunched and accelerated by a radio frequency cavity system up to about 5 MeV for instance.

The linear accelerator aims at accelerating the beam coming from the radiation source to the final energy of at least about 30 MeV.

In one embodiment, the device is arranged for carry out scanning of the target volume. During scanning, successive regions are irradiated, each under FLASH conditions. Between successive FLASH irradiations, the target region is moved by resetting the trajectories of the beam in the beam delivery system. A volume is thus covered by a series of independent FLASH voxels during the same fraction.

In an embodiment, the linear accelerator comprises radio frequency accelerating structures capable of accelerating the radiation beam (i.e. the required total charge) in the required overall time.

In an embodiment, the linear accelerator is arranged for accelerating one to at least ten trains of particles bunches, each train approximately 250 ns long and each containing 250 particles bunches of 1 nC each, within 10 ms, thus fulfilling FLASH conditions. Preferably, the linear accelerator is arranged for operating in burst mode in a frequency up to about 1000 Hz and preferably between about 100 and 1000 Hz.

In one embodiment, the linear accelerator is arranged to accelerate the beam with an accelerating gradient with beam in excess of at least about 35 MeV/m.

In an embodiment, the linear accelerator is operating on a frequency chosen from the list comprising X-band, C-band or S-band, preferably, X-band.

In an embodiment, the linear accelerator is a linac based on multi-GHz radio frequency systems.

Preferably, the linear accelerator is a high current linear accelerator, for instance a high current X-band linac. For instance, the total charge needed for a treatment of 2500 nC before collimation, is made in ten trains of particles bunches of 250 nC/train of particles bunches. A train of bunches is 250 ns long so the current is 1 A.

In an embodiment, the device comprises means for stabilizing the beam to achieve a maximum variation of the radiation dose of about +/−2% over one month. For instance, the beam will be stabilized through a feedback. Just before delivering to the patient the beam will travel on a straight ahead trajectory by turning the main dipole off (if the delivery module comprises energy-based separating means by using magnetic spectrometer). A sequence of radiation pulses (train of particles bunches) will be captured by diagnostics and machine parameters and adjusted to bring the charge to the required values. Once completed the beam will be directed towards the patient. There will also be a feedback during treatment by monitoring dose over each radiation pulse (train of particles bunches) and correcting deviations on subsequent radiation pulses (trains of particles bunches).

In one embodiment, the device is arranged for providing a dose uniformity within the target volume of at least of at least about 80%, preferably at least about 85%, at least about 15 cm deep in the tissue, preferably about 20 cm. The main advantage is to have less intra-tumor variations of the dose.

In one embodiment, the dose is delivered in 3 to 20 radiation pulses, preferably 10 radiation pulses. Advantageously, the number of pulses should be as low as possible, ideally one to three. The number of radiation pulses depends on the amount of charge per (radio frequency) pulse, and said amount of charge is mainly limited by the capabilities of the radiation source. It also depends on stability of transport of the beam through the linear accelerator to preferably about 1 A. Finally, it is also related to the cost of the installed linear accelerator powering system.

In one embodiment, the device comprises at least two beam delivery modules, each delivery module being arranged for treating one patient. In this embodiment, multiple treatment rooms can be supplied by a single electrons source and a single linear accelerator. It is known that the bulk of the equipment cost is in the system through to the end of the linear accelerator, i.e. from the radiation source until the linear accelerator included. Adding more modules delivery is highly cost effective. Also since the treatment time is much shorter than the patient setup time, multiple delivery modules the throughput of the facility goes up directly proportional to the number of delivery modules.

The present invention further relates to a method for treating a tumor target volume of a patient with ultra-high dose rate radiation, the method comprising:

Providing a device according to the invention;
Setting the device so as to generate an accelerated radiation beam having a predetermined energy between about 50 MeV and about 250 MeV, more preferably between about 120 MeV and about 150 MeV, to deliver an ultra-high dose rate radiation dose of at least about 10 Gy, preferably up to about 25 Gy, preferably up to about 35 Gy, more preferably up to about 40 Gy, during an overall time less than about 200 ms, preferably less than about 100 ms, preferably less than about 50 ms, preferably less than about 10 ms;
Delivering the radiation dose to a target volume of at least about 30 $cm^3$, preferably between about 30 $cm^3$ and about 1000 $cm^3$ and/or a target volume located at least about 5 cm deep in the tissue of the patient, preferably between about 5 cm and about 25 cm.

The particular advantages of the method are similar to the ones of the device of the invention described herein and will thus not be repeated here.

In an embodiment, the treatment comprises
Delivering the radiation dose to a target volume located at least about 10 cm deep in the tissue of the patient and/or target volume having a diameter of at least about 10 cm.

In one embodiment, the treatment comprises administering the dose in radiation pulses of accelerated radiation beam, said dose having at least about 2 Gy per radiation pulse, preferably at least about 5 Gy per radiation pulse, more preferably at least about 10 Gy per radiation pulse, with a dose rate in the radiation pulse of at least about $10^6$ Gy/sec, and preferably a total number of radiation pulses below 10, more preferably below 3. In other words, the treatment comprises administering the dose in conditions needed for obtaining a FLASH effect in large field irradiation (diameter above or equal to 10 cm) i.e. a dose in the radiation pulse of at least 2 Gy and preferably more, dose rate in the pulse of $10^6$ Gy/sec and preferable more, an overall treatment time for a dose of 25 Gy in the range of few milliseconds (below 50 ms and preferably below 10 ms) and a total number of radiation pulses below 10 and preferably below 3.

The dose can be delivered in any number of radiation pulses. Preferably the number of radiation pulse is below 20. In one embodiment, the treatment comprises administering the dose delivered in 1 to 10 radiation pulses, e.g. 1, 2, 3, 4, 5, 6, 7, 8, 9 or 10 radiation pulses.

In one embodiment, the treatment comprises administering the total dose in one fraction.

In other embodiment, the treatment comprises administering the dose divided in several fractions, for instance 2 or 3 fractions. Preferably, the number of fractions is less than 3, which is appropriate to obtain a FLASH effect.

In the present invention, a large target volume means a target volume having at least a diameter of about 5 cm (equal or superior), diameter meaning one dimension across the entire the target volume if the target volume is not spherical. The target volume can be of any size or shape. For instance, the diameter is comprised between about 5 cm and about 30 cm, preferably between about 5 cm and about 20 cm.

In the present invention, a deep seated target volume means a target volume located at least about 5 cm deep in the tissue, preferably between about 5 cm and 30 cm deep in the tissue, preferably between about 5 cm and about 25 cm and preferably between 10 cm and 20 cm.

In the present invention, ultra-high dose rate radiation means FLASH radiotherapy or FLASH Therapy. FLASH radiotherapy can be defined as a radiotherapy treatment where a sparing of healthy tissue is obtained at least equivalent to about 33% less dose as compared to conventional RT dose, while preserving intact the effect on tumors As used herein, the term "treating" or "treatment" refers to administering a treatment to a tumor or the subject diagnosed with a tumor. The treatment can be administered in an amount or therapeutic dose that is sufficient or effective to kill tumor cells (i.e., a therapeutically effective amount), slow the growth of the tumor, reduce the size of the tumor, or eliminate the tumor from the subject entirely. The term also includes selecting a treatment or treatment plan, and providing treatment options to a healthcare provider or the subject.

In some embodiments, the method for treating a tumor target volume of a patient with ultra-high dose rate radiation, as described herein, further comprises administrating one or more additional therapy selected from the group comprising a therapeutic agent (such as chemotherapy, radioprotectors or radiosensitizers), an immune modulator agent (such as e.g. immune checkpoint inhibitor molecule, an immune checkpoint activator molecule, a chemokine inhibitor, an inhibitor of macrophage migration inhibitory factor (MIF), a growth factor, a cytokine, an interleukin, an interferon, an antibody that binds to an immune system cell, such as a bispecific antibody that binds to T-cells and a tumor antigen, a cellular immune modulator such as a CAR-T cell, a vaccine, an oncolytic virus, and any combination thereof), a senolytic agent, a radiosensitizer, a nanoparticle or combinations thereof. The additional therapy can be administered concomitantly, or as an adjuvant, or in a neo-adjuvant procedure.

As used herein, the term "about" applies to numeric values or ranges of numeric values and refers to a range of numbers that one of skill in the art would consider equivalent to the recited values, i.e. plus or minus ten percent. For example, "about 10 cm" refers to 10 cm+/−10%, i.e. 9 cm to 11 cm. In the present invention, a dose refers to the total radiation dose in Gy delivered to the patient. A dose can be administered in several fractions.

As used herein the term "patient" is well-recognized in the art, and refers to a mammal, including dog, cat, rat, mouse, monkey, pig, and, most preferably, a human. In some embodiments, the patient is a patient in need of treatment or a patient suffering from cancer. The term does not denote a particular age or sex. Thus, adult and newborn patients, whether male or female, are intended to be covered.

As used herein, the term "radio wave pulse" refers to the pulse of radio wave used in the linear accelerator. The linear accelerator uses radio wave pulses of microwave power to accelerate a radiation beam from a radiation source, for instance an electron beam from an electron source. For instance, these radio wave pulses are around 250 ns long and can be repeated with repetition rate of 1 kHz, that is with a period of 1 ms, in burst mode. Preferably, for long term operation the optimal repetition rate is about 100 Hz. For example, the frequency of the microwaves is X-band, specifically 12 GHz, but can also be C (5.7 GHz) or S (3 GHz) band.

As used herein, the terms "radiation pulse" refer to the pulse of particles after the linear accelerator. Each pulse accelerates at least a train of particles bunches, for instance electron bunches if the radiation beam is an electron beam or proton bunches if the radiation beam is a proton beam. For example, the particles bunches are about 10 ps long and come every 1 ns, so that there are 250 particles bunches in a 250 ns radio wave pulse. Each particles bunch has a charge of 1 nC giving a total charge of 2500 nC (before collimation) and an average current during the pulse of 1 A.

The embodiments describe herein for the device also apply to the methods according to the present invention mutatis mutandis.

The embodiments describe herein for any one of the method also apply to the device according to the present invention mutatis mutandis.

BRIEF DESCRIPTION OF THE DRAWINGS

Further particular advantages and features of the invention will become more apparent from the following non-limitative description of at least one embodiment of the invention which will refer to the accompanying drawings, wherein.

DETAILED DESCRIPTION OF THE INVENTION

The present detailed description is intended to illustrate the invention in a non-limitative manner since any feature of an embodiment may be combined with any other feature of a different embodiment in an advantageous manner.

Figure 1:
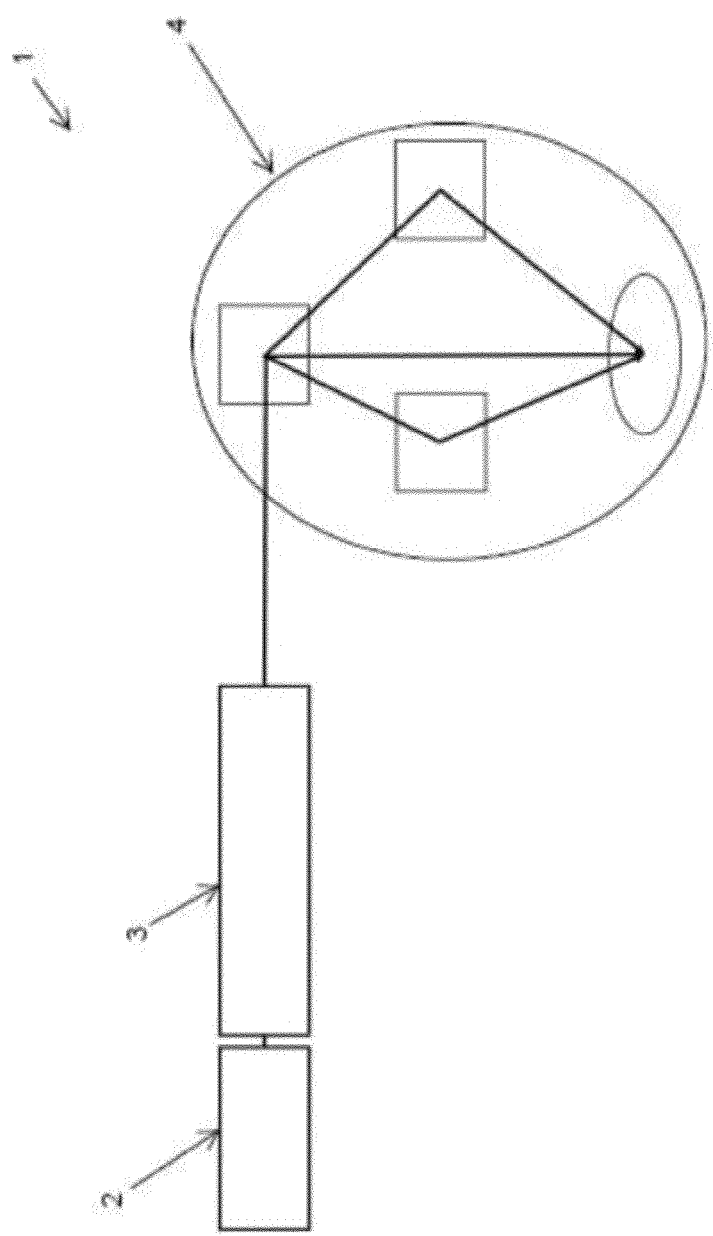
FIGS. 1 and 2 represent a device according to the present invention according to a first embodiment.
Figure 2:
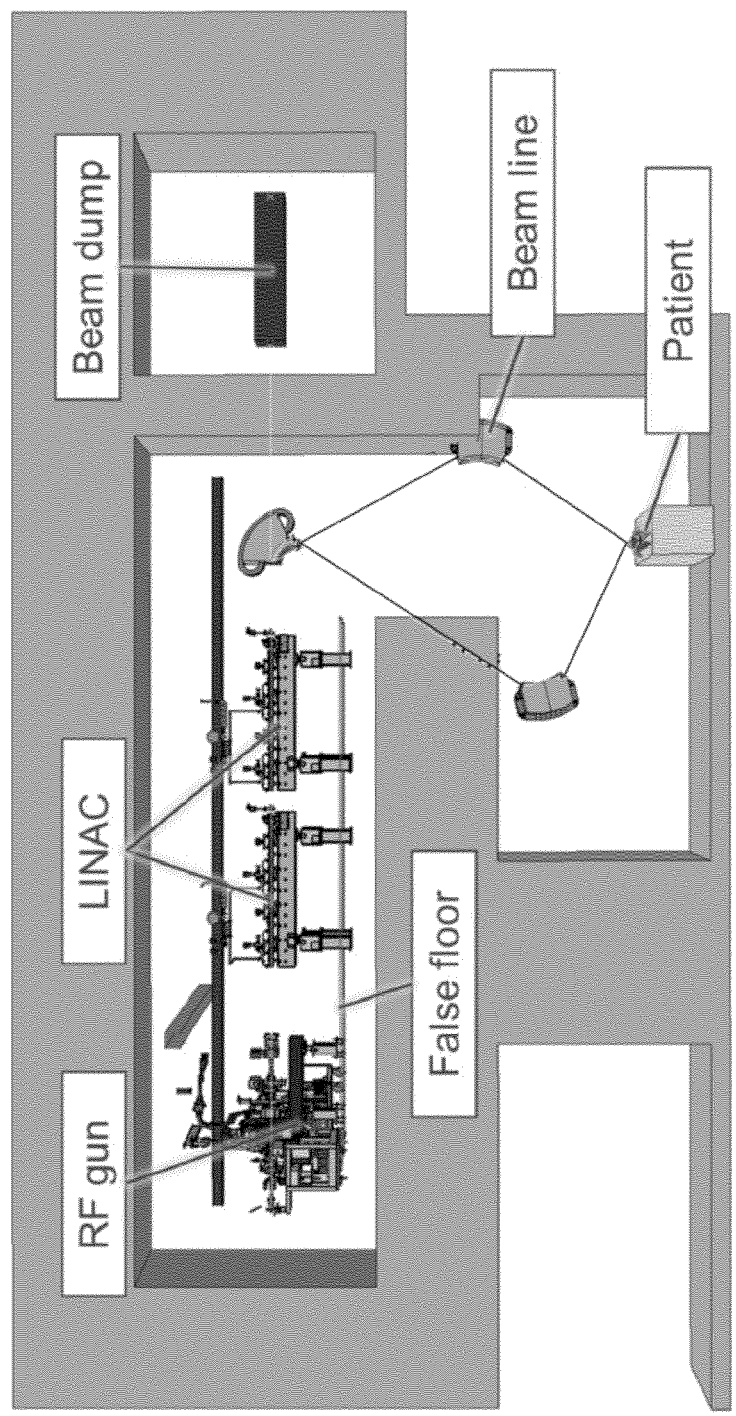

FIGS. 1 and 2 represent a device 1 according to the present invention according to a first embodiment.

The device 1 comprises a radiation source 2, a linear accelerator 2 and a beam delivery module 3. The device 1 is arranged for delivering a radiation dose to a target volume 5 of a patient (not shown in figures).

The radiation source 2 is a high current electron source, in particular a Radio-frequency laser-driven photo-injector. The photo injector produces the electron bunches and accelerates them to an energy where they are relativistic. It consists of a set of coupled resonant cavities which are powered by a klystron modulator system. A short laser pulse impinges on the back plane of the first cavity causing the emission of electrons, to form a bunch, by the photoelectric effect. The back plane of the photocathode is coated with $Cs_2Te$ for increased quantum efficiency and a laser with 262 nm wavelength is used. Microwave fields of approximately 110 MV/m accelerate the bunch. Successive laser pulses during an rf pulse form a train of bunches. Successive rf pulses give multiple trains.

In the embodiment represented in FIGS. 1 and 2, the photo injector operates at S-band, specifically 2.9985 GHz, has 1.5 cells and accelerates the beam up to 5 MeV. The photoinjector is powered by a klystron and requires approximately 30 MW of input power.

The photo injector produces bunches of a charge of 0.308 nC with a spacing of ⅓ ns between bunches, giving an average current during the pulse of approximately 1 A. There are 953 bunches per train. Each bunch is approximately 300 micrometers long.

The linear accelerator 3, or linac, is a high current X-Band linac. In the embodiment represented in FIGS. 1 and 2, the linac has parameters of eight half meter long accelerating structures, operating with a beam-loaded gradient of 35 MV/m. The linac is powered by two 50 MW peak power X-band klystrons and radio-frequency pulse compressors. The linac accelerates the beam up to the treatment energy. In the present example, the linac consists of repeated rf units which consists of a klystron modulator, an rf pulse compressor, a waveguide network and multiple accelerating structures.

In the embodiment represented in FIGS. 1 and 2, the linac accelerates the beam from the 5 MeV coming out of the injector, to adjustable energies up to a maximum of 140 MeV. The linac operates in X-band, specifically 11.994 GHz. An rf unit consists of a modulator driving a 50 MW klystron, the pulse compressor and four accelerating structures. The pulse compressor gives a factor of 2.8 in power gain. Each accelerating structure is 0.5 long and operates in the 2π/3 phase advance travelling wave mode. Each rf unit gives the beam 70 MeV of energy gain. The accelerating gradient, with the nominal beam current of approximately 1 A, is up to 35 MV/m. Two rf units give a maximum energy of 140 MeV.

A combination of magnetic elements and rf focusing controls the properties of the beam. The accelerating structures are equipped with higher-order-mode damping to transport the high current beam without instabilities.

The beam delivery module consists of normal conducting magnets; one main dipole magnet to deflect and separate the different energy beams, dipole magnets to give the trajectories that enter the patient at the defined angles and quadrupole magnets to guide the beam, then control the irradiation spot size of the beam entering the patient.

The beam delivery system represented in the present example consists of a separator magnet and bending magnet (as separating means) to respectively separate the single accelerated beam in multiple beam lines and direct said multiple beam lines on the patient. The separator magnet is used to direct trains of discrete energies of the single beam into the multiple beam lines. The multiple beam lines are divergent after the separator magnet. Bending magnets near the middle of the individual lines direct the particle trajectories back to the target volume. The quadrupoles in each the beamlines also expand the beam from the mm size in the linac to the final treatment dimensions which can be larger than 15 cm.

In the embodiment represented in FIGS. 1 and 2, the separator magnet has a length of 55.5 cm and a half aperture of 15 mm. The bending magnets have a length of 80 cm and a half aperture of 25 mm.

The quadrupoles in the beamlines have lengths of 20 cm and half apertures of 18 to 35 mm.

Figure 3:
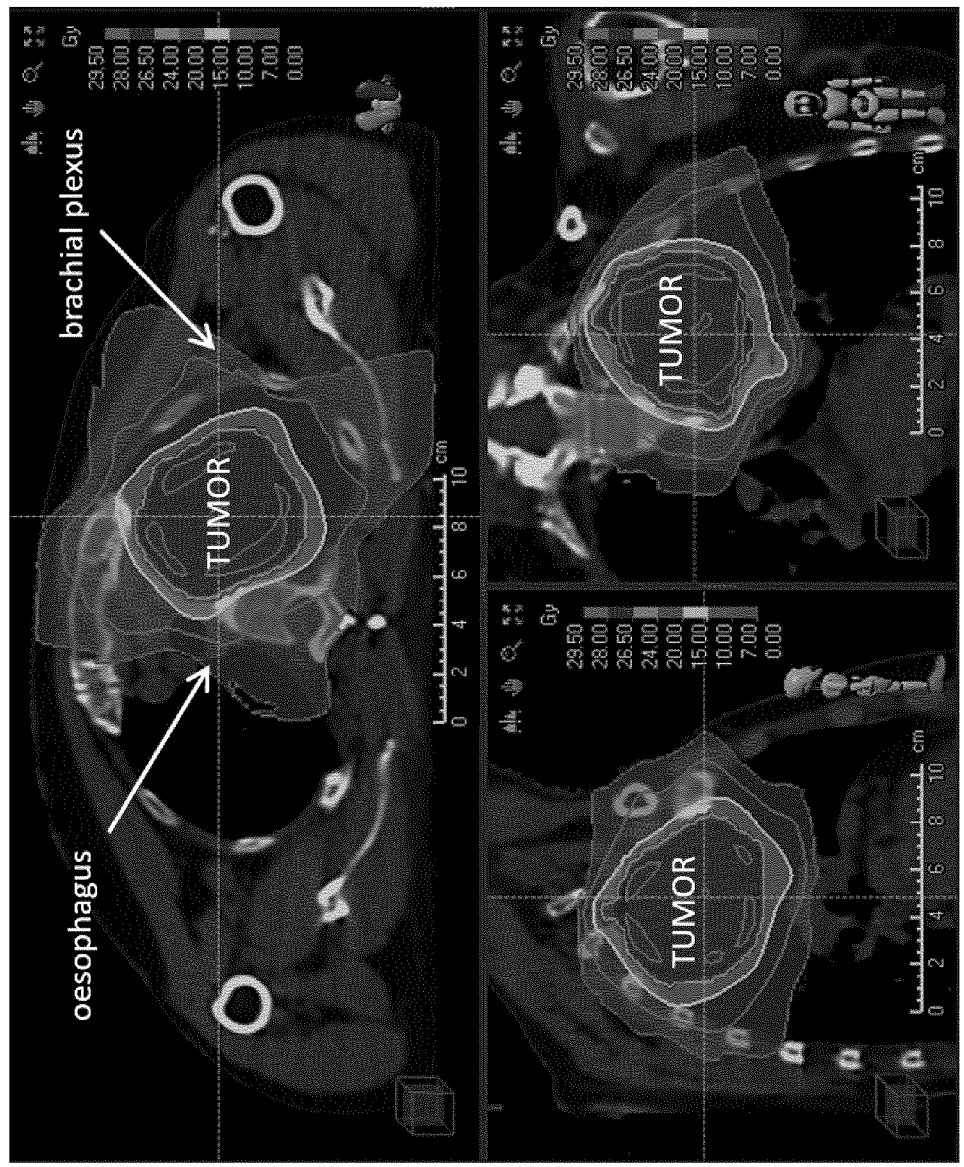
FIG. 3 illustrates a simulation of a FLASH-Therapy with the present invention in a patient with a large (10 cm diameter) lung cancer.

FIG. 3 represents simulation of a FLASH-Therapy with the present invention in a patient with a large lung cancer. In the present case, a device according to the present invention was used to simulate a FLASH-RT treatment in a T4-N0 lung cancer patient having a 10 cm large tumor size.

In this FIG. 3, due to the proximity of the tumor with critical organs such as brachial plexus and oesophagus, as shown in FIG. 2, this patient could only receive 46 Gy in 23 fractions in conventional RT, which gave a tumor biological equivalent dose (BED) of 46 Gy. The simulation of a FLASH treatment using a device according to the present invention allowed to deliver a single dose of 28 Gy safely. This corresponds to a highly curative BED of 115 Gy for the tumor. Advantageously, this simulation integrates a normal tissue sparing factor of 33% due to the FLASH conditions.

Figure 4:
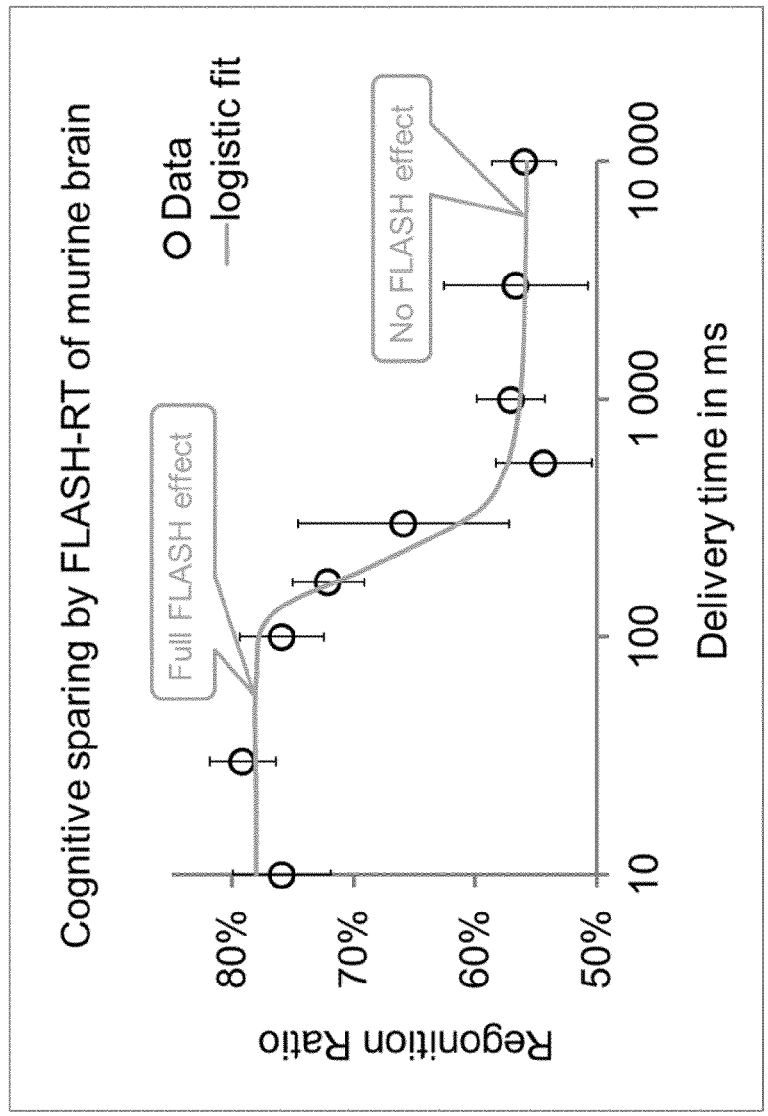
FIG. 4 shows the evolution of the cognitive sparing of murine brain after 10 Gy brain irradiation by a 6 MeV electron beam.

FIG. 4 shows the evolution of the cognitive sparing of murine brain after 10 Gy brain irradiation by a 6 MeV electron beam. The experimental data are adapted from P. Montay-Gruel et al, Radiother Oncol, 2017; 124:365-9. The curve is a logistic fit through the data. The figure shows how the effect on neuroprotection as evaluated by novel Object Recognition tests (vertical axis: Recognition ratio in percent) varies with overall time for delivering 10 Gy (horizontal axis in ms). It clearly highlights the necessity of delivering the irradiation in less than 200 ms, preferably less than 100 ms, more preferably less than 50 ms to beneficiate of the FLASH protection effect as proposed by the present invention.

Figure 5:
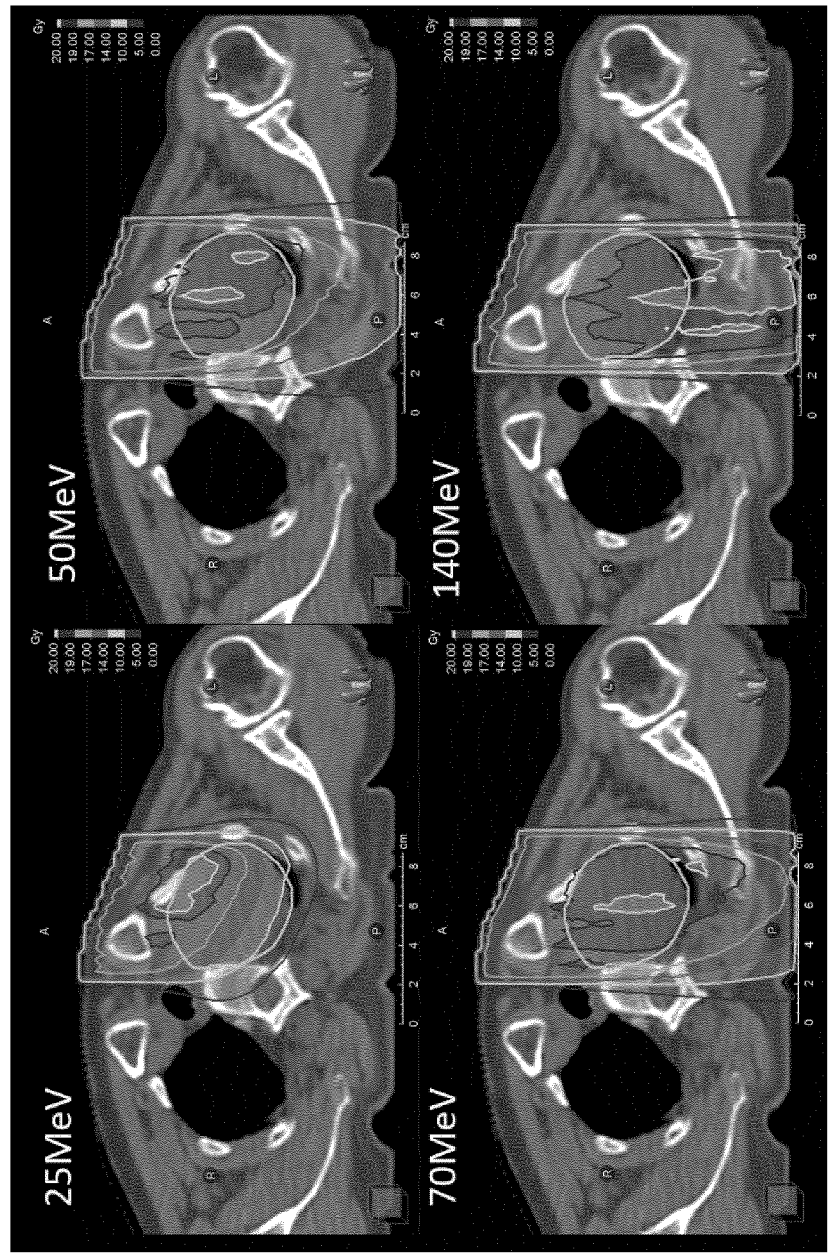
FIG. 5 shows dosimetry simulations for the penetration into human thorax of the irradiation by single electron beam in the range of energies 25 MeV to 140 MeV.

FIG. 5 shows dosimetry simulations for the penetration into human thorax of the irradiation by single electron beam in the range of energies 25 MeV to 140 MeV. The thin lines corresponds to the dose variations (isodoses) for an irradiation of 20 Gy at the depth of maximum. The thick line represents an 8 cm diameter tumour volume at 11 cm depth. The FIG. 5 illustrates the need to achieve an energy of more than 50 MeV to avoid an underdosage of the deeper part of the tumour as it is described in the present invention.

While the embodiments have been described in conjunction with a number of embodiments, it is evident that many alternatives, modifications and variations would be or are apparent to those of ordinary skill in the applicable arts. Accordingly, this disclosure is intended to embrace all such alternatives, modifications, equivalents and variations that are within the scope of this disclosure. This for example particularly the case regarding the different apparatuses which can be used.

REFERENCE NUMBERS

1 Device according to a first embodiment
2 Radiation source
3 Linear accelerator
4 Beam delivery module

The invention claimed is:

1. A device for providing an ultra-high dose rate radiation treatment to a patient, the device comprising:
a radiation source arranged to provide a radiation beam;
a single linear accelerator arranged to accelerate said radiation beam until reaching a predetermined energy; and
a beam delivery module arranged to deliver the accelerated radiation beam from said single linear accelerator toward the patient to treat a target volume with a radiation dose, wherein:
the device is arranged to generate the accelerated radiation beam having the predetermined energy between about 50 MeV and about 250 MeV, and to deliver an ultra-high dose rate radiation dose of at least about 10 Gy, during an overall time less than about 200 ms,
the device is arranged for generating a radiation field for treating the target volume of at least about 30 cm$^3$ with said ultra-high dose rate radiation dose, and/or treating a target volume located at least about 5 cm deep in the tissue of the patient with said ultra-high dose rate radiation dose, and
the single linear accelerator is arranged to generate a single accelerated beam comprising multiple trains of particle bunches, the beam delivery module is arranged to separate the single accelerated radiation beam into a plurality of accelerated beam lines separated by a determined angle, and subsequently focus each of said beam lines toward the patient to arrive simultaneously on the target volume, and each beam line corresponds to multiple trains of particle bunches,
wherein the beam delivery module is arranged to separate the accelerated radiation beam into a plurality of accelerated beam lines with a radiation dose of between 7 Gy and 20 Gy per beam delivered during said overall time, and
wherein the beam delivery module includes a magnetic spectrometer.

2. The device according to claim 1, wherein each train has energy which differs by at least about 10%, and/or each beam line has an energy of at least about 50 MeV.

3. The device according to claim 1, wherein the device is arranged to control the conformal irradiation of the beam arriving on the target volume.

4. The device according to claim 1, wherein said radiation dose comprises radiation pulses of the accelerated radiation beam, each radiation pulse comprising at least one particle bunch, and the device is arranged for delivering the ultra-high-dose rate radiation dose with at least about 2 Gy per radiation pulse, with a dose rate in the pulse of at least about $10^6$ Gy/sec.

5. The device according to claim 1, wherein the device is arranged for delivering the dose with a homogeneity of target volume coverage of at least about 85%.

6. The device according to claim 1, wherein the radiation source is an electron source.

7. The device according to claim 1, wherein the radiation source is arranged for delivering the radiation dose in a sequence of a train of particle bunches with a capability of up to ten trains of particle bunches of 250 nC each in said overall time.

8. The device according to claim 1, wherein said accelerated beam is a very high energy electron (VHEE) beam with a charge of at least about 1000nC.

9. The device according to claim 1, wherein the radiation source comprises at least one of a radio-frequency laser-driven injector, and a thermionic injector.

10. The device according to claim 1, wherein the single linear accelerator comprises radio frequency accelerating structures arranged to accelerate the radiation beam in the required overall time.

11. The device according to claim 1, wherein the single linear accelerator is operating on a frequency including at least one of X-band, C-band and S-band.

12. The device according to claim 1, wherein the device is arranged to perform scanning of the target volume.

13. The device according to claim 1, wherein the device comprises at least two beam delivery modules, and each delivery module is arranged for treating one patient.

14. The device according to claim 1, wherein the device is arranged to generate the accelerated radiation beam having the predetermined energy between about 120 MeV and about 150 MeV, to deliver the ultra-high dose rate radiation dose up to about 25 Gy, during an overall time less than about 100 ms.

15. The device according to claim 1, wherein the device is arranged to generate the accelerated radiation to deliver the ultra-high dose rate radiation dose of up to about 35 Gy during an overall time less than about 50 ms.

16. The device according to claim 1, wherein the device is arranged to generate the accelerated radiation beam to deliver the ultra-high dose rate radiation dose during an overall time less than about 10 ms.

17. The device according to claim 1, wherein the device is arranged to generate the radiation field for treating the target volume between about 30 $cm^3$ and about 1000 $cm^3$ with said ultra-high dose rate radiation dose, and/or treat the target volume located between about 5 cm and about 25 cm deep in the tissue of the patient with said ultra-high dose rate radiation dose.

\* \* \* \* \*